United States Patent [19]

Hawkins et al.

[11] Patent Number: 4,951,825
[45] Date of Patent: Aug. 28, 1990

[54] APPARATUS FOR CLASSIFYING PARTICULATE MATERIAL

[75] Inventors: Albert P. Hawkins, Caulfiled; David Santwyk-Anderson, Hurstbridge, both of Australia

[73] Assignee: CRA Services Ltd., Melbourne, Australia

[21] Appl. No.: 380,101

[22] Filed: May 25, 1989

Related U.S. Application Data

[63] Continuation of Ser. No. 82,636, filed as PCT AU86/00284 on Sep. 30, 1986, published as WO87/01975 on Apr. 9, 1987, abandoned.

[30] Foreign Application Priority Data

Sep. 30, 1985 [AU] Australia .............................. PH2670

[51] Int. Cl.$^5$ ..................... B07C 5/342; B07C 5/36
[52] U.S. Cl. ..................... 209/558; 209/580; 209/586; 209/644; 209/905; 356/30; 364/526
[58] Field of Search ............ 209/555, 556, 558, 563, 209/564, 576, 577, 580–582, 586, 587, 643, 644, 905; 356/30, 317; 364/526, 579, 580

[56] References Cited

U.S. PATENT DOCUMENTS

| | | | |
|---|---|---|---|
| 1,945,395 | 1/1934 | Cockrell | 209/587 |
| 2,054,319 | 9/1936 | Hanson | 209/581 |
| 2,054,320 | 9/1936 | Hanson | 209/581 |
| 2,131,095 | 9/1938 | Cox | 209/581 X |
| 2,131,096 | 9/1938 | Cox | 209/581 X |
| 2,152,758 | 4/1939 | Cox | 209/905 X |
| 2,244,826 | 6/1941 | Cox | 209/587 X |
| 2,325,665 | 8/1943 | Cox | 209/581 |
| 2,474,230 | 6/1949 | Cox | 250/223 R |
| 3,058,588 | 10/1962 | Palmquist | 209/581 X |
| 3,060,790 | 10/1962 | Ward | 364/526 X |
| 3,366,236 | 1/1968 | Breazeale | 209/564 |
| 3,380,586 | 4/1968 | Frobese et al. | 209/581 X |
| 3,385,434 | 5/1968 | Nelson | 209/581 X |
| 3,565,249 | 2/1971 | Codding | 209/587 X |
| 3,878,384 | 4/1975 | Bowker | 364/570 |
| 4,057,146 | 11/1977 | Castaneda et al. | 209/581 |
| 4,143,770 | 3/1979 | Grimmell et al. | 209/580 X |
| 4,154,672 | 5/1979 | Wiley et al. | 209/905 X |
| 4,186,838 | 2/1980 | Levitt et al. | 209/581 |
| 4,278,538 | 7/1981 | Lawrence et al. | 209/581 X |
| 4,280,625 | 7/1981 | Grobbelaar et al. | 209/582 |
| 4,454,029 | 6/1984 | Codding | 209/581 |
| 4,515,275 | 5/1985 | Mills et al. | 209/580 X |
| 4,663,522 | 5/1987 | Welbourn et al. | 209/576 X |

FOREIGN PATENT DOCUMENTS

| | | | |
|---|---|---|---|
| 60-178322 | 9/1985 | Japan | 364/526 |
| 1097387 | 6/1984 | U.S.S.R. | 209/587 |
| 941301 | 11/1963 | United Kingdom | |
| 2165644 | 4/1986 | United Kingdom | 209/581 |

Primary Examiner—Johnny D. Cherry
Assistant Examiner—Edward M. Wacyra
Attorney, Agent, or Firm—Nixon & Vanderhye

[57] ABSTRACT

Apparatus for classifying particulate material on a particle by particle basis according to the extent to which the particles possess certain attributes, such as the presence of particular colors when viewed from different directions. A particle feeder (12) feeds particles past an inspection system (13) which inspects each particle and derives signals which are a measure of a plurality of attributes of the particle. A separation or airblast mechanism (14) operates to direct particles to multiple outlets (15) according to the signals derived by the inspection system (13). This operation is controlled by a signal processor which can store a plurality of sets of specific values of attributes each set of which is typical of one of a plurality of particular classes into which the particulate material is to be classified and can compare subsequently measured sets of values of attributes of successive particles with the stored sets to determine a closest match with one of the particular classes.

12 Claims, 12 Drawing Sheets

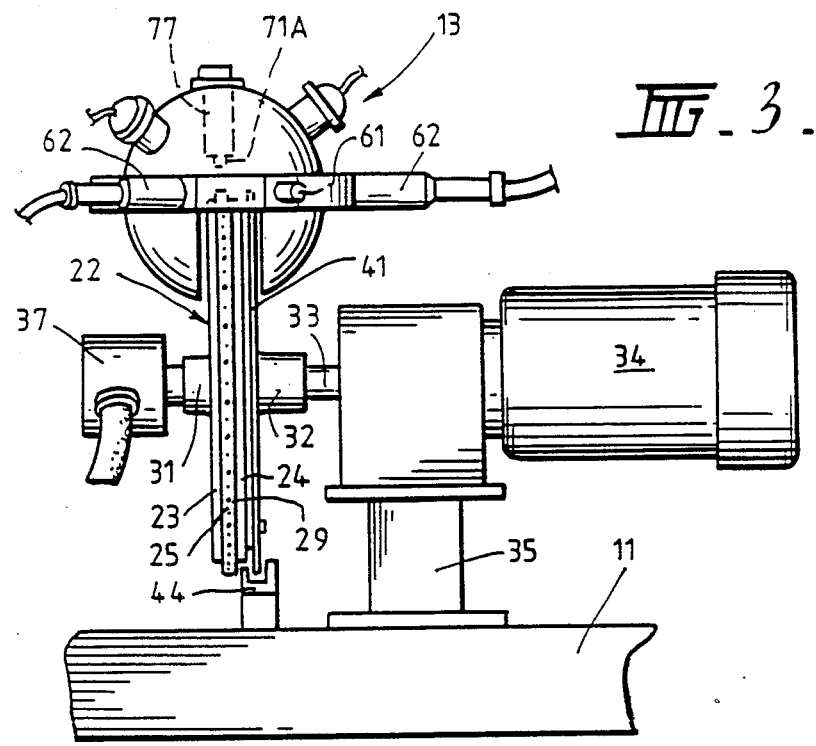
FIG_3.
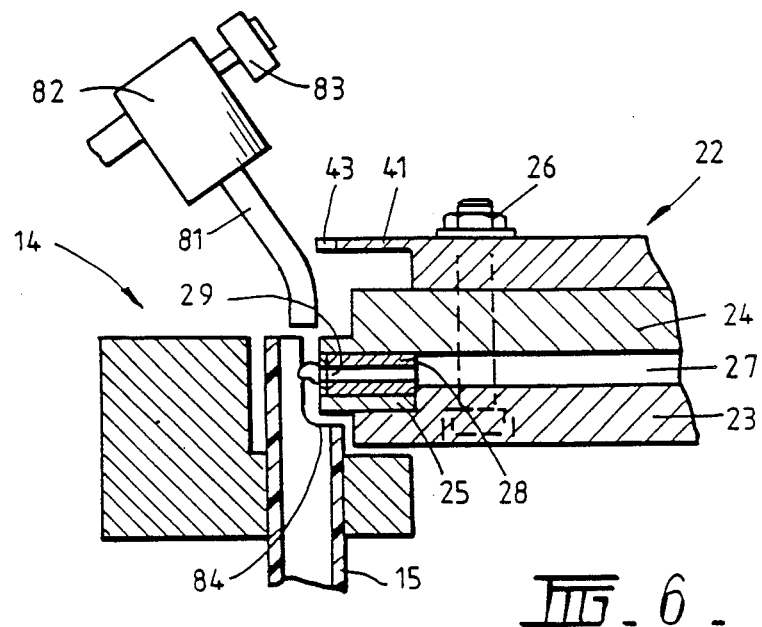
FIG_6.

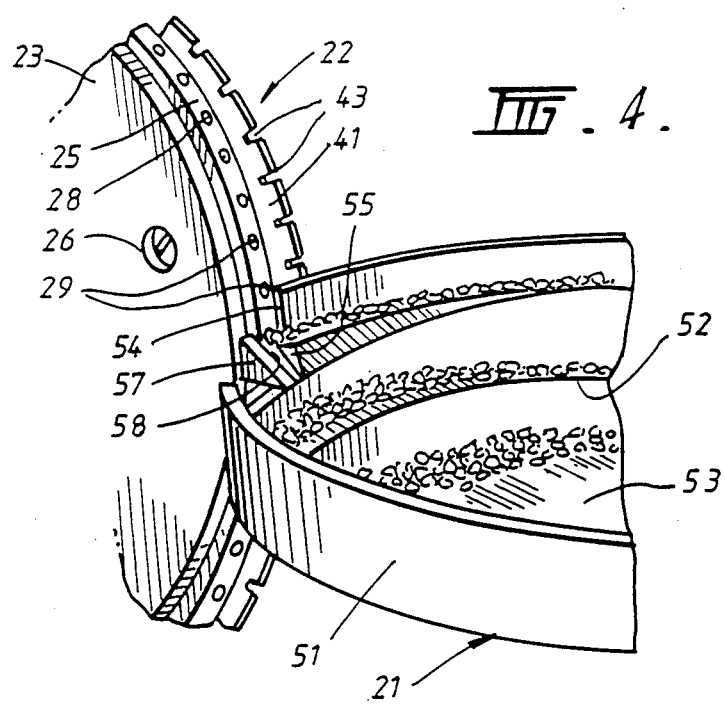
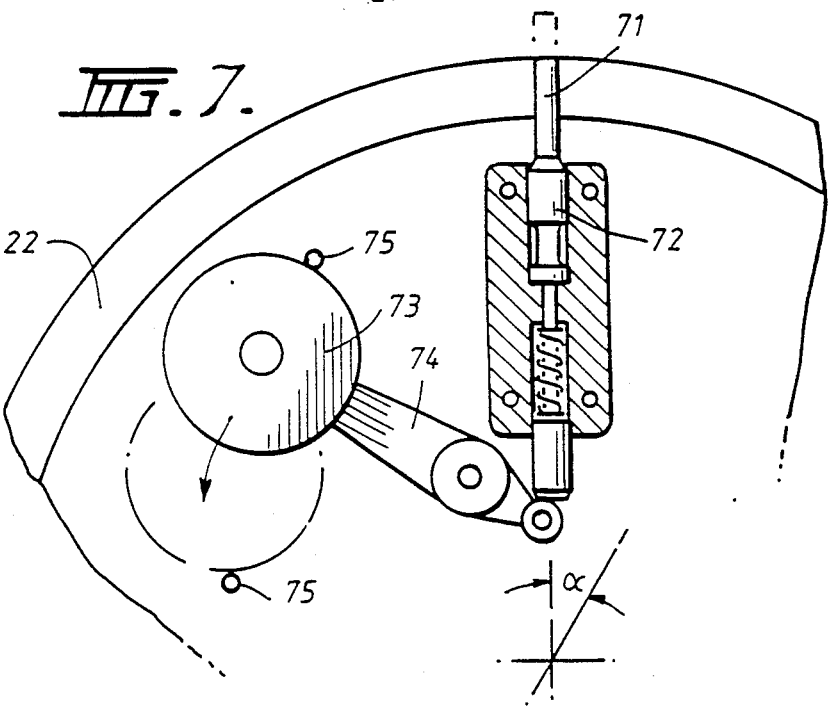

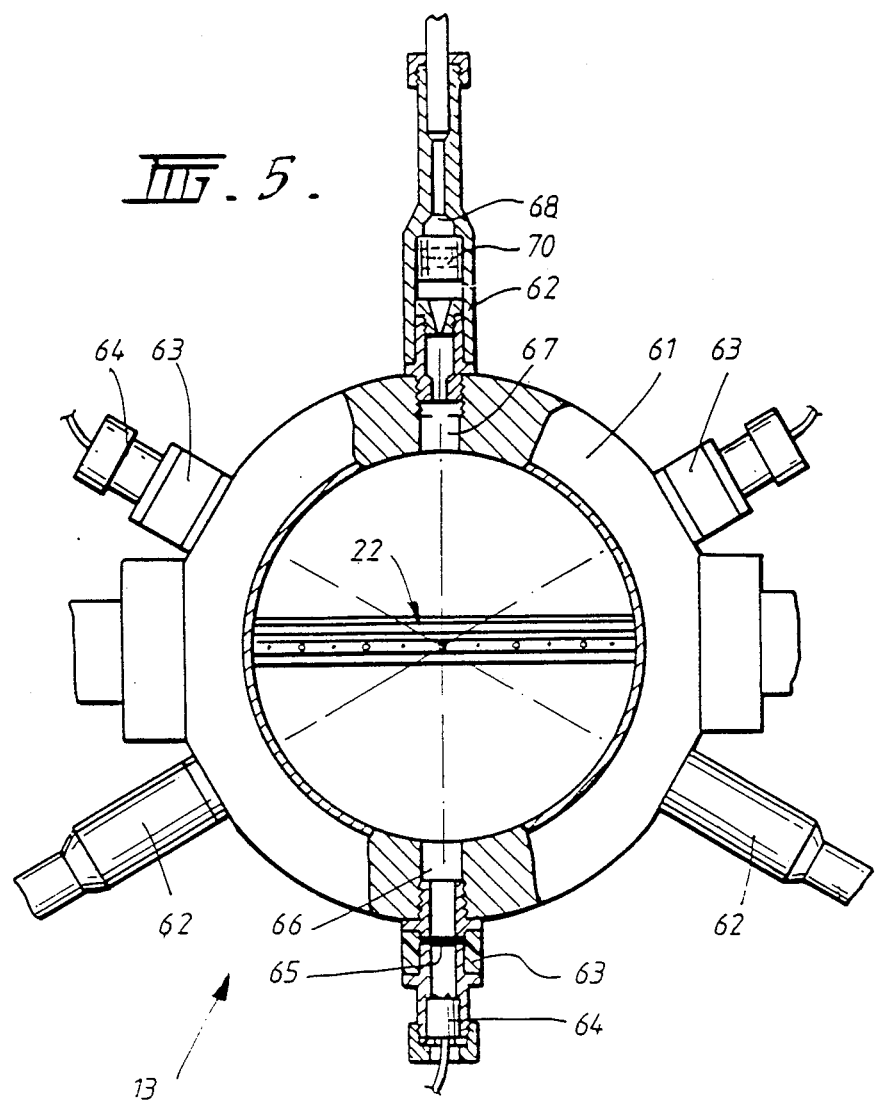

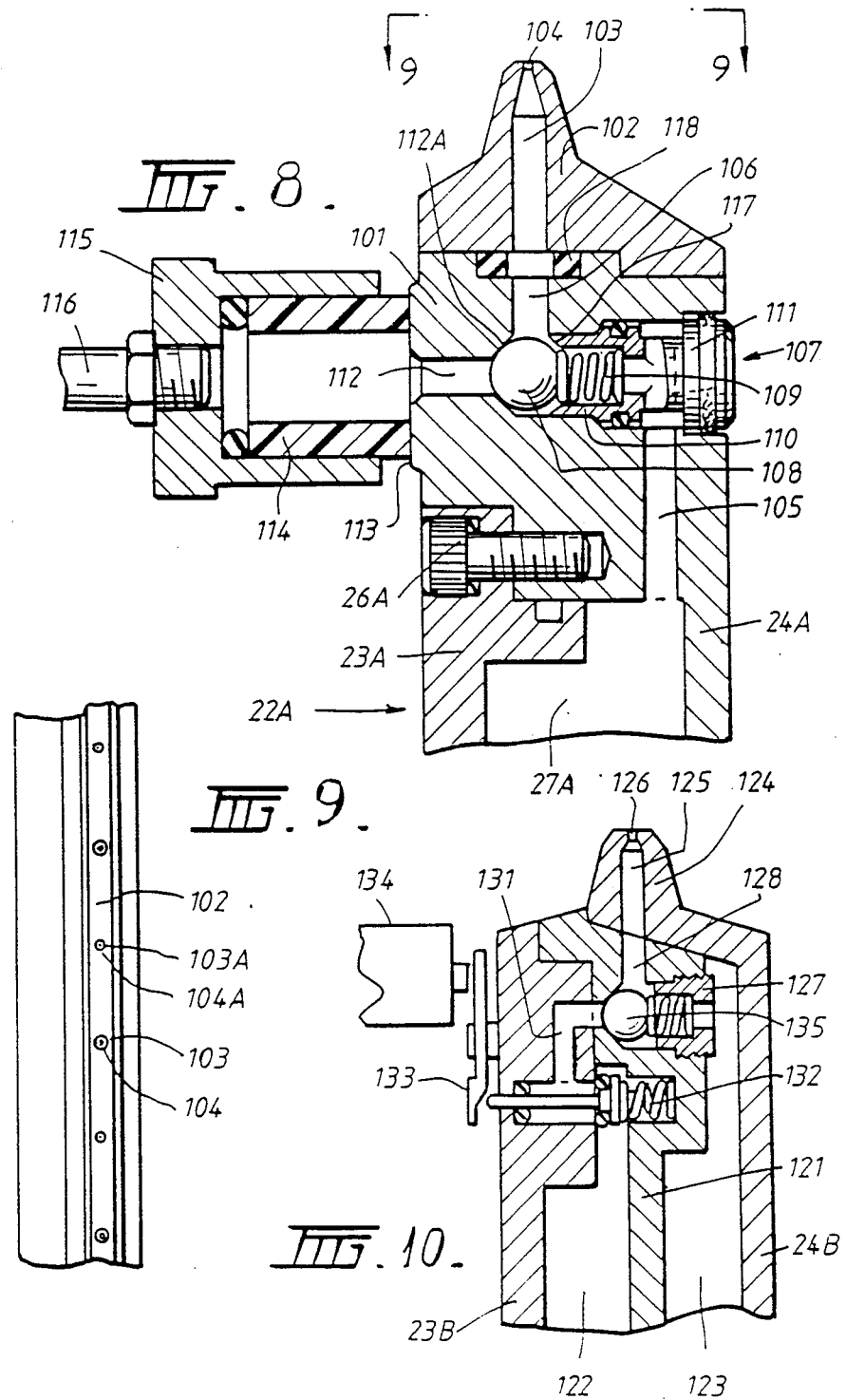

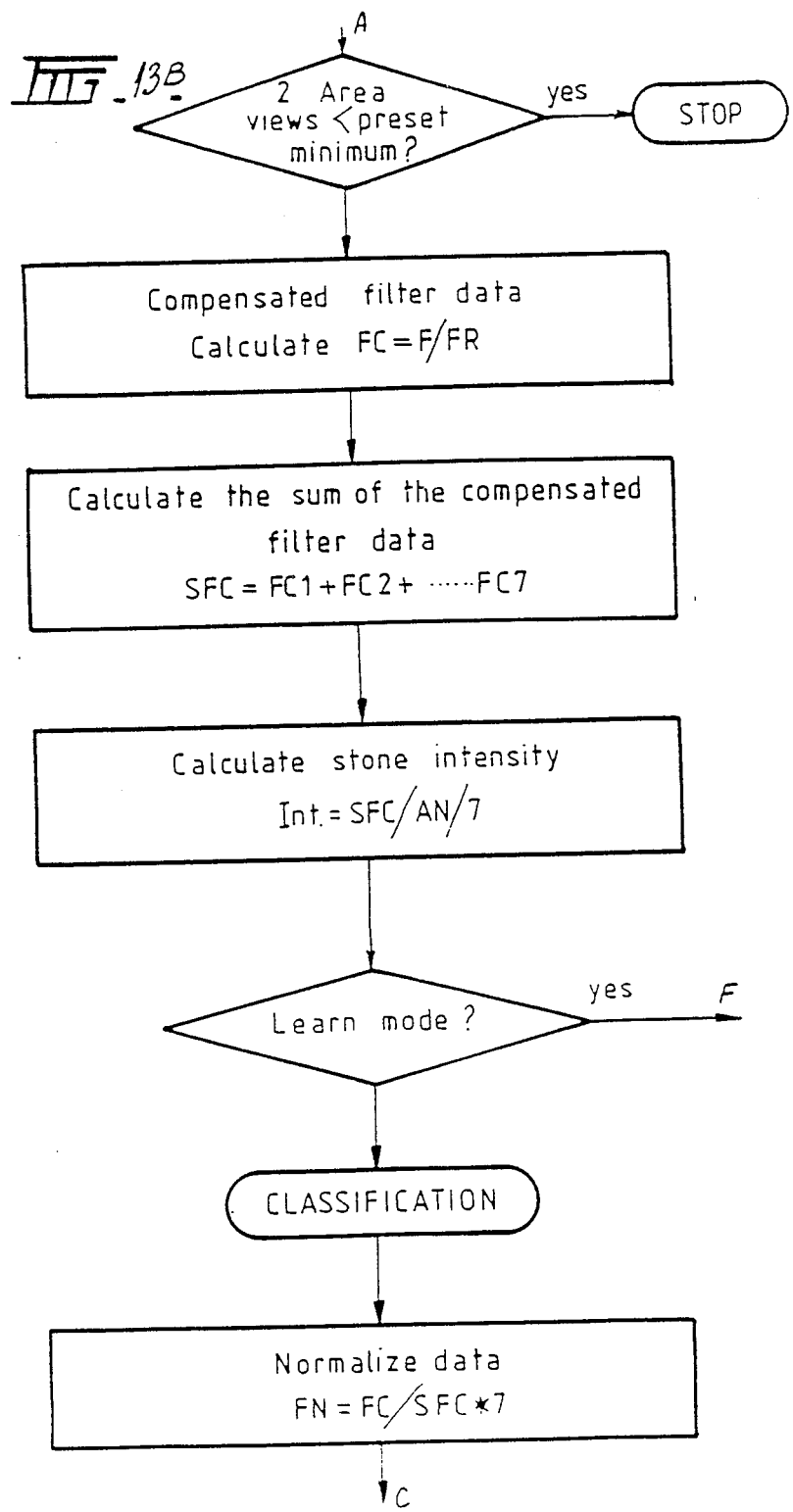

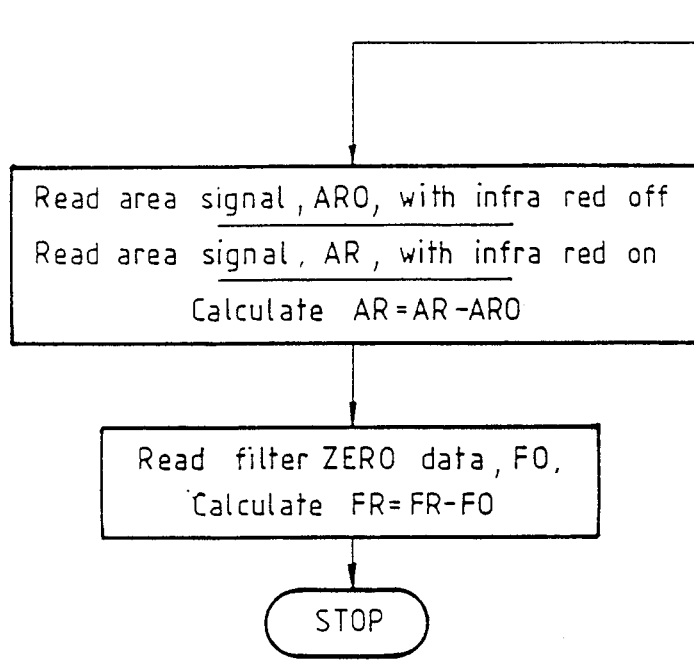
FIG_13E

APPARATUS FOR CLASSIFYING PARTICULATE MATERIAL

This is a continuation of application Ser. No. 07/082,636, filed as PCT U886/00284 on Sep. 30, 1986, published as WO87/01975 on Apr. 9, 1987, now abandoned.

TECHNICAL FIELD

This invention provides a novel kind of classifier for classifying particulate material on a particle by particle basis according to the extent to which the particles possess certain attributes of interest.

The invention has arisen from a program to develop a classifier for automatically classifying rough diamonds but from the ensuing description it will be appreciated that classifiers constructed in accordance with the invention could be applied to the classification of other particulate materials such as gem stones of various kinds, mineral ores or even food particles. As used herein the terms "particulate material" and "particles" are to be interpreted broadly as extending to any body of material comprised of separable, individual or discrete objects. The particulate material may for example be crushed ore in which case the articles may be ore rocks of any size, a body of gem stones, or even a body of fruit, vegatables or grain.

DISCLOSURE OF THE INVENTION

According to the invention there is provided apparatus for classifying particulate material, comprising:

particle feed means to feed particulate material to be classified particle by particle along a feed path;

inspection means to inspect each particle fed along the feed path and to derive signals which are a measure of a plurality of attributes of that particle;

classifier means operable to direct the particles from said path selectively to multiple outlets; and control means to control operation of the classifier means in accordance with the signals derived from the inspection means.

Preferably the control means includes signal processing means having means to store a plurality of sets of specific values of attributes each set of which is typical of one of the plurality of particular classes into which the particulate material is to be classified, and means to compare subsequently measured sets of values of attributes of successive particles with the stored sets and to determine a closest match with one of said particular classes.

Preferably further the processing means can be set to enable the said plurality of sets of specific values to be stored by feeding pre-sorted stones through the system whereby said specific values are derived by the inspection means operating on those pre-sorted stones.

Said attributes may comprise the presence of particular colours when viewed from a plurality of directions.

BRIEF DESCRIPTION OF THE DRAWINGS.

In order that the invention may be more fully explained one particular classifier which is particularly suited to classifying rough diamonds will now be described in some detail with reference to the accompanying drawings in which:

FIG. 3 is a view on the line 3—3 in FIG. 2;

FIG. 4 is a perspective view in the direction of arrow A in FIG. 2;

FIG. 5 is a cross-section on line 5—5 in FIG. 2;

FIG. 6 is a cross-section on the line 6—6 in FIG. 2;

FIG. 7 shows a colour reference system extension and retraction mechanism;

FIG. 8 illustrates an alternative kind of particle separation means for the classifier;

FIG. 9 is a view on the line 9—9 in FIG. 8;

FIG. 10 illustrates a further alternative kind of particle separation means;

BEST MODE OF CARRYING OUT THE INVENTION

Figure 1:
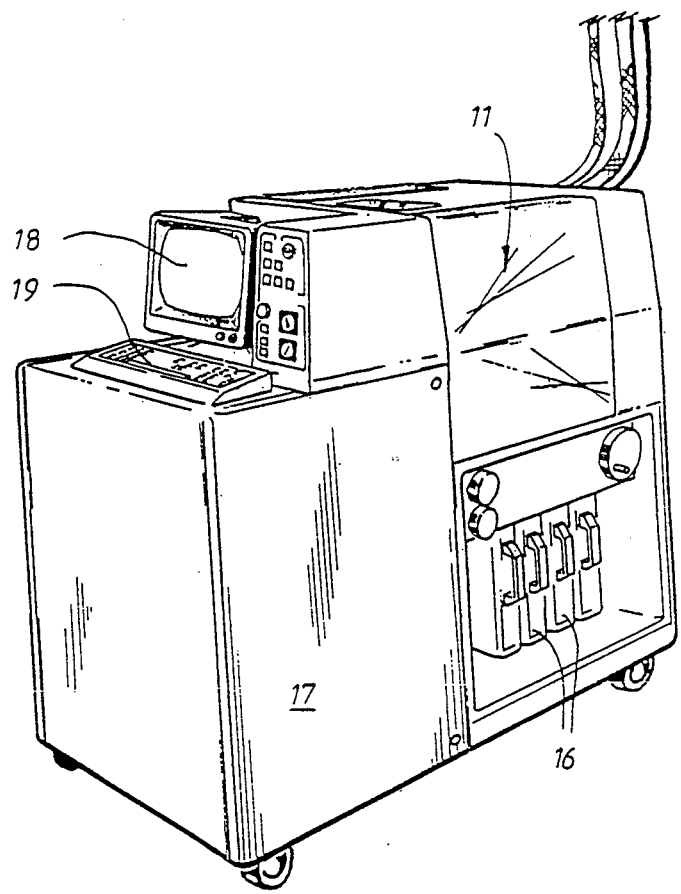
FIG. 1 is perspective view of the classifier.

The illustrated classifier has been designed to measure attributes of small objects such as rough diamonds and to produce multiple product streams according to the extent to which the measured attributes match those for a number of predetermined classes. The attributes for the various classes can be "taught" to the machine by introducing to the machine pre-sorted objects, a class at a time.

In the case of diamond classification, the classes are separate colour categories of rough diamonds—the product of light from an integrating sphere surrounding the diamond at an inspection zone, the light entering the body of the gem, being selectively absorbed in accordance with its colour and being re-emitted. Measurement is made of this emitted light as viewed by an optical system with colour selective outputs, as will be described in more detail below.

In order to achieve the required measurement accuracy, it is necessary to define quite precisely the position of each diamond in the field of view of the optics. Further in order to achieve high speed multi-class identification, it is necessary to have a means of keeping a precise track of each particle past a series of possible product stream outlets so that the particles can be accurately routed to any one of the possible outlet streams. In the illustrated apparatus, both of these required features are realized by use of a suction pick-up presentation system, using a rotating vacuum union to allow suction to be applied to a large number of suction ports on the periphery of a rotating wheel. The diamond stones can thus be picked up individually and pass through an inspection zone and thence to one of a series of outlet ducts disposed around the periphery of the wheel, an appropriate outlet duct being selected by an electronic processor depending on the closeness of match of the colour measurements to pre-learned classes.

Referring now to the drawings, the classifier comprises a wheeled frame 11 which at one end carries the diamond feed system 12, the optical viewing system 13, air blast means 14 for removing the diamonds from the feed means at various air blast stations chosen according to the measurements derived from the inspection means 13 and a series of product outlets ducts 15 extending to collection bins 16. The other end of the main frame carries a cabinet 17 to house an electronic processor, a monitor 18 and a keyboard 19 which is connected to the electronic processor.

The feed system 12 comprises a vibratory bowl feeder 21 and a rotary wheel structure 22. The wheel structure 22 is in the form of a hollow wheel comprised of circular side plates 23, 24 clamped about a peripheral rim member 25 by means of clamping bolts 26 so as to leave a hollow interior space 27. Rim member 25 carries a series of circumferentially spaced tubular bushes 28 defining suction ports 29 extending radially inwardly through the rim to the hollow interior space 27.

The side plate 23, has an outwardly extending hollow hub 31. Said plate 24 has a hub 32 connected to the output shaft 33 of a gear reduction motor 34 which is mounted on a pedestal 35 on the main frame 11. The wheel is thus mounted for rotation about a horizontal axis on operation of the geared motor. The hollow hub 31 connects via a rotating vacuum seal union 37 to a vacuum pump whereby the hollow interior space 27 of the wheel structure can be evacuated to apply suction to the suction ports 29 as the wheel structure is rotated by operation of the geared motor 34.

The wheel structure 22 also comprises a notched disc 41 which is fastened to the side plate 24 by the fastening studs 26. The outer periphery of disc 41, which is generally adjacent the rim of the wheel structure, is provided with a series of circumferentially spaced radial notches 43 which are aligned with the suction ports 29 on the rim i.e. there is one notch adjacent each of the suction ports. A slotted opto-switch 44 is mounted on frame 11 at the bottom of the wheel structure so as to receive the periphery of slotted disc 41 and to produce output pulses as the notches in that disc pass the swtich. These output pulses are thus an accurate measure of angular incremental rotations of the wheel structure.

Vibratory bowl feeder 21 has a bowl 51 having a stepped peripheral wall to define a ramp 52 which spirals upwardly from the bottom floor 53 of the bowl to a slot 54 in the upper part of the peripheral wall of the bowl. The bowl feeder is mounted so that the slot 54 receives the outer rim portion of the suction wheel 22 generally at the level of the horizontal axis of rotation of the wheel so that the wheel rim moves upwardly through the slot due to rotation of the wheel. Thus the suction ports 29 move successively upwardly through slot adjacent the discharge end of the ramp 52 of the vibratory bowl feeder.

The bowl is vibrated such that the diamond particles move in a stream up the ramp and are delivered from the ramp in a generally horizontal stream transverse to the direction of upward movement of the suction ports on rotation of the wheel. Individual particles become attached to the suction ports by suction and are then transported in an arcuate path by the rotary movement of the wheel. The speed of stone flow around the ramp is matched approximately to the take up rate of the wheel.

The monolayer distribution and horizontal motion of the stones on the vibrating feeder ensure that one stone at a time is available for pick up and that orientation of the stones is favourable for subsequent inspection. Specifically the stones tend to lie flat on their largest faces which are thus aligned transversely to the rim of the wheel so that they tend to be picked up with their points or edges presented to the suction port. Accordingly, the stones stand proud from the rim of the wheel rather than lying flat against it. This allows for better optical viewing of the stones.

The upward motion of the wheel tends to automatically clear potential jamming points and gaps. Minimization of multiple pick-ups is also ensured by the shaping of the vibratory bowl feeder at the pick-up zone. As indicated in FIG. 4 the discharge end of the ramp 52 terminates at a vertical ledge 55. This ledge is spaced back about one particle length from the line of the suction ports so that at pick up, the stones are tipping around the sharp corner at the intersection of the ramp and the vertical ledge face. This tipping movement of the stones promotes separation between successive stones at the time that the leading stone is picked up. This overcomes any tendency for successive stones to bank up or ride up one on the other and helps to minimize multiple pick-ups.

Vertical ledge face 55 forms one side face of a chute by which any stones not picked up by the wheel are directed back into the bottom of the vibratory bowl. The other side of the chute is defined by a vertical triangular wall 57 and the chute has an inwardly and downwardly sloping floor 58.

The upper part of the feed wheel projects into the optical viewing system 13. This viewing system comprises a hemispherical bowl fitted with three quartz iodide lamps to flood the stones to be examined with intense white light. The bottom of the bowl (sometimes referred to as an integration sphere), is fitted with a ring 61 on which there are mounted three optical viewers 62 arranged at equal circumferential spacing around the ring and three infra-red background emitters 63 disposed one diametrically opposite each of the three viewers 62. Each infra-red background emitter has three infra-red light emitting diodes 64 projecting light through a diffusing screen 65 aligned with an aperture 66 in the ring 61. The diametrically opposite optical viewer 62 has a microscope objective lens system 70 providing an almost parallel field of view through a ring aperture 67 to the infra-red background emitter. The microscope lens system focusses onto an optics aperture 68 from which collected light is transmitted by means of a fibre optic light guide (now shown).

The optical viewing system provides three views of each stone spaced 120° apart to ensure adequate coverage of each particle.

Referencing of the optical scan is carried out by a white reflection standard which is positioned at one of the pick up points on the rim of the wheel and is set in place in the scan zone once per revolution by a spring and weight system which is illustrated in FIG. 7. The white reference standard 71 is carried on a spring loaded rod 72 which is extended through an aperature in the wheel rim against its spring loading by the action of a swinging weight 73 and lever 74 as the colour reference moves through the range of angular movement indicated by the angle α in FIG. 7. Swinging movement of the weight 73 is limited by two stops 75. Another of the pick-up positions is left blank to provide a "no stone" dark reference measurement.

Figure 2:
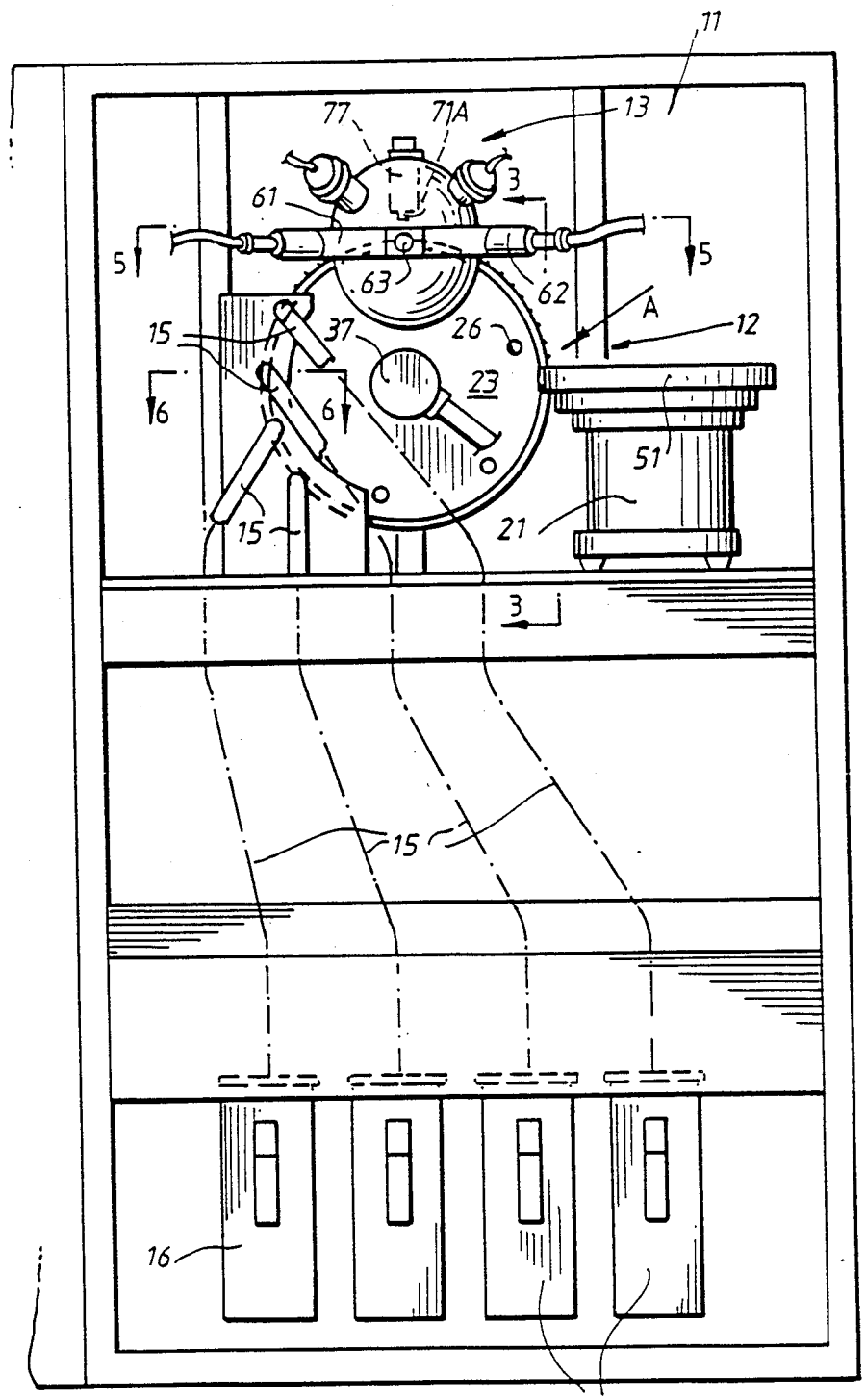
FIG. 2 is a side view of some major components of the classifier.

An alternative manner of providing a white reflection standard shown in FIGS. 2 and 3 by broken lines indicating a white reference standard 71A carried on a pneumatic cylinder unit 77 mounted externally of the wheel and operable to move the referenced standard into the optical scan field of view at the appropriate times.

For colour sorting, the sort parameter is derived from sampling the re-emitted light from the stone (relative to the white standard) at a number of wavelength points in the visible spectrum. Typically there may be a choice of seven visible channels and a further infra-red channel.

In this case there would be eight channels from each of the three views providing twenty-four separate detector outputs for each stone.

In each view, a stone passing the background throws a shadow onto the respective infra-red detector which reduces in response in proportion to the shadow area of the stone for that particular view. This output is primarily used to normalize for stone size to allow a more accurate luminosity response (to neutral stones, grey, black etc.), independent of stone size. The seven visible channels are measured and compared with white reflectance adjusted to subtract the background, and compensated for stone area variations.

The wavelength split is carried out by fibre optic light guides, one set for each of the three views. A large input bundle is subdivided on a random basis so that it becomes eight guides at the output. Each of the eight ends goes through a different colour filter to a photo-detector. The outputs of the photo-detectors are fed to the processor which determines the correct classification for each particular stone and according to the determined classification the stone is blown from the wheel into one of the discharge ducts 15 by the air blast means 14 which is located at the side of the wheel opposite the vibratory feeders. The air blast means comprises a series of air blast nozzles directed transversely across the rim of the wheel and spaced circumferentially of the wheel. The air blast nozzles are supplied with air through electrically operated valves under the control of the processor.

FIG. 6 shows one of the air blast nozzles 81 supplied with air through a valve 82 actuated by a controller 83. The nozzle is directed towards the inlet end of a respective discharge duct 15 which is notched at 84 to fit around the projecting rim of the suction wheel. If the processor determines that a particular stone is to be directed to that particular outlet or discharge tube, the air blast nozzle is actuated as the stone passes between the end of the tube and the nozzle so that it is blasted down the tube. The precise timing necessary to keep an accurate track of each particle as it passes the series of possible product stream outlets is achieved by reference to the notches 43 on disc 41 on the vacuum wheel.

FIGS. 8 and 9 illustrate a modification whereby the stones can be positively ejected from the wheel by interrupting the application of suction to the respective suction ports and applying fluid under pressure to those ports so as to eject the stones therefrom. In this case, the rotary wheel structure 22A comprises side plates 23A, 24A clamped together by means of clamping bolts 26A so as to leave a hollow interior space 27A. In this case, however, the outer margins of the side plates are modified so that the wheel space 27A is closed by an outer peripheral flange portion 101 of the side plate 24A which carries an outer rim member 102 provided with circumferentially spaced radial passages 103 defining the suction ports 104. Passages 105, 106 formed within flange portion 101 provide for communication between the passages 103 and the evacuated interior 27A of the wheel subject to the condition of a spring loaded valve denoted generally as 107. Valve 107 comprises a ball 108 biased by a spring 109 disposed within a bush 110 held in position by a retaining stud 111.

A series of circumferentially spaced passages 112 are formed in the flange portion 101 to extend inwardly from a said face 113 of the flange portion to communicate with the valve chambers of the valves 107. Flange face 113 is engaged by a tubular sliding seal member 114 fitted within an air supply nozzle 115 supplied with pressurized air from a supply line 116.

The ball 108 of each valve 107 is normally spring biased against a valve seat 112A at the inner end of the respective air inlet passage 112 so as to seal off the air inlet passage 112 and open the valve for the application of suction from the space 27A to the suction ports 104 via the passages 105 and 106. When a stone is to be ejected, a valve in the air supply line 116 is actuated at the correct time to supply air under pressure through the sliding seal member 114 to the respective air inlet passage 112. The pressurized air forces the valve ball 108 against its spring bias to engage a valve seat 117 at the end of valve bush 110 so disrupting the application of suction to the respective port 104 and applying a jet of pressurized air to that port so as to eject the stone. The seating of ball 108 on valve seat 117 closes the passage 105 against ingress of pressurized air so that the application of suction to the other suction ports is not affected.

With the modification illustrated in FIGS. 8 and 9, the stone collection ducts 15 are rearranged to extend radially from the wheel. The positive ejection is much more accurate and the collection ducts can be smaller and more closely spaced, so permitting classification into more categories if necessary. This arrangement also permits lower air consumption and quieter operation and it promotes clearing of the suction ports against clogging with small chips.

Rim member 102 is formed with an alternative set of radial passages 103A and suction ports 104A of a smaller size than the suction ports 104 and the rim can be angularly adjusted on the wheel flange portion 101 so as to allow either of the sets of passages 103, 103A to be indexed with the passages 106. Thus, either the relative large suction ports 104 or the smaller ports 104A can be brought into operation according to the size of stones to be classified. Annular seals 118 are provided in the outer face of the flange portion 101 to seal the interconnection between the passages 106 and the passages 103 or 103A when the outer rim member 102 is properly indexed.

FIG. 10 illustrates an alternative wheel construction in which the wheel side plates 23B, 24B are separated by a central dividing plate 121 which divides the interior of the wheel into two chambers 122, 123. Chamber 123 is subject to vacuum pressure and chamber 122 is supplied with air under high pressure. Wheel plate 24B is formed with an outwardly projecting peripheral rim 124 provided with radial passages 125 and suction ports 126. Suction is normally applied to the suction ports 126 via a valve bush 127 and radial passage 128 in the central plate 121. A passage 131 is provided in wheel plate 23B to enable high pressure air to be admitted to the suction ports when a spring loaded valve 132 is actuated through an actuating cam 133 on operation of a solenoid 134. A spring loaded ball 135 normally seals the passage 131 when vacuum is being applied to the suction ports but this ball is pushed back when high pressure air is admitted to the ports to seal against the bush 127 so as to seal off the vacuum system against admission of the high pressure air. Instead of operating valve 132 by an external fixed solenoid, it would be possible to employ an internally mounted solenoid coil, supplied with power through slip rings at the rotational mounting of the wheel and activated remotely by means of a Hall Effect device with appropriate circuitry.

As previously indicated, the processor can be "taught" an appropriate number of classes by introducing to the machine pre-sorted objects a class at a time. The seven colour channels of the processor are normalized and matching criteria are used to establish if a particular stone is within allowable closeness to a pre-taught class. There are three levels of criteria:
 (i) the stone must be within a class tolerance;
 (ii) ranking of classes must be adhered to so that if class overlaps are encountered the stone will be classified into the most valuable stream; and
 (iii) if no ranking is applied the stone goes to the class nearest in terms of the sum of magnitude of differences between the stone wavelength responses and the average of the class wavelength responses.

The class with the minimum sum is selected as the interest class, provided of course that it is within tolerance as set out in criterion (i).

Figure 11:
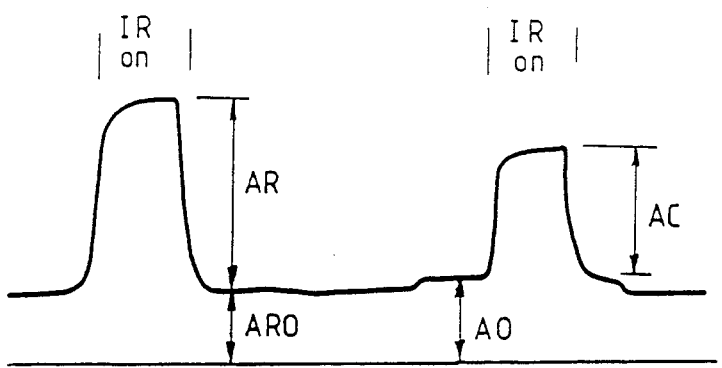
FIGS. 11 and 12 illustrate signal forms obtained in the inspection system of the classifier.
Figure 12:
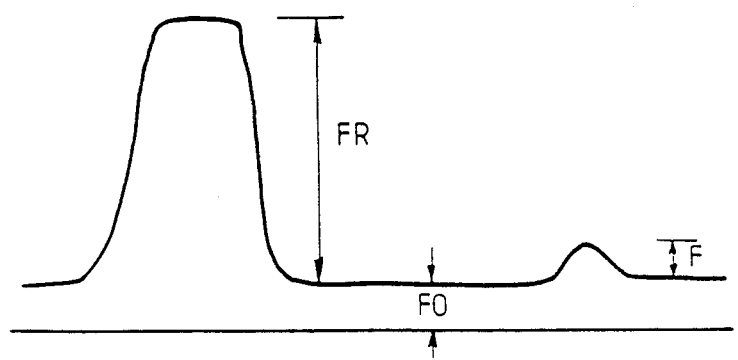
Figure 13A:
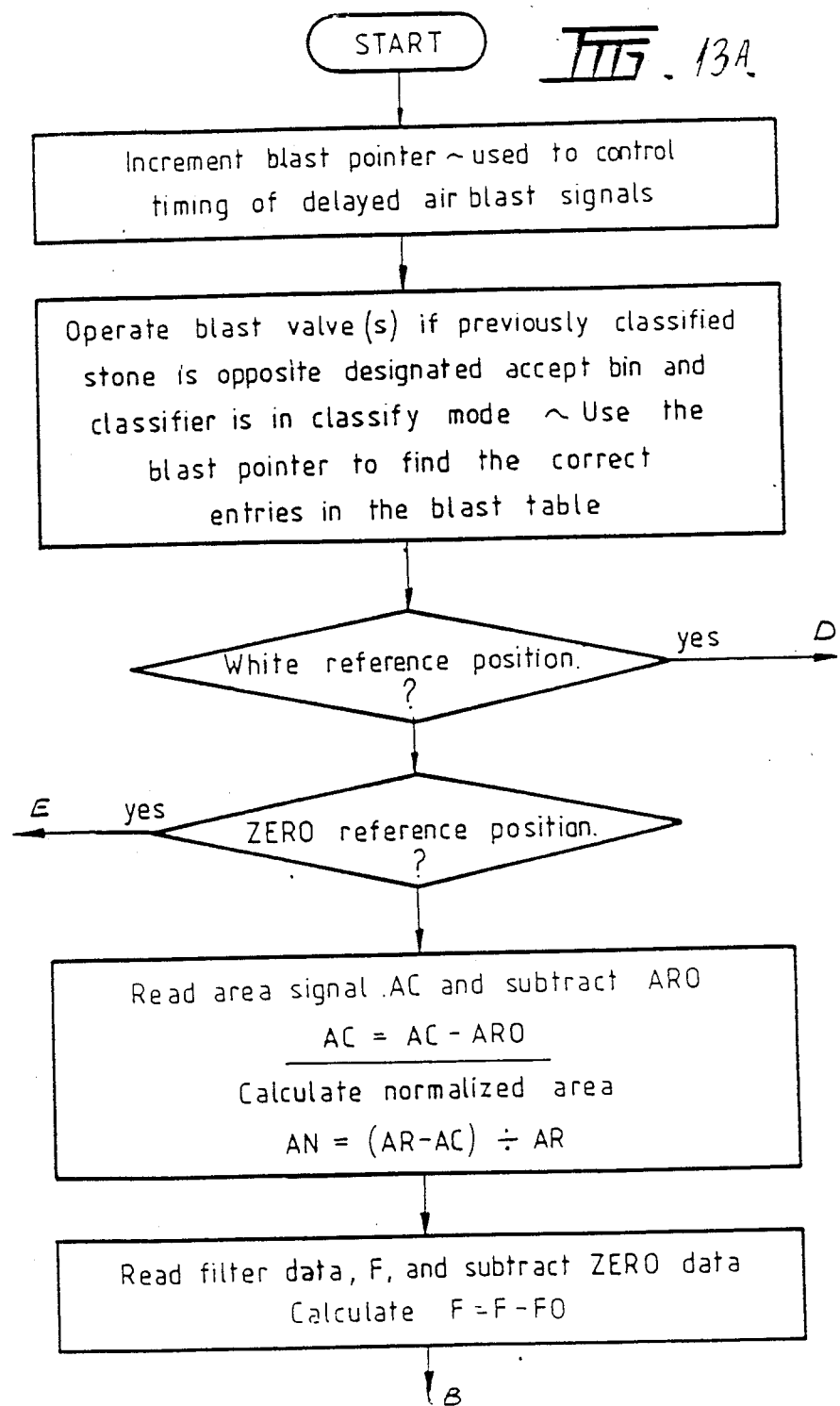
FIGS. 13A–13E collectively represent a flow sheet for the classification routines carried out by the classifier.
Figure 13C:
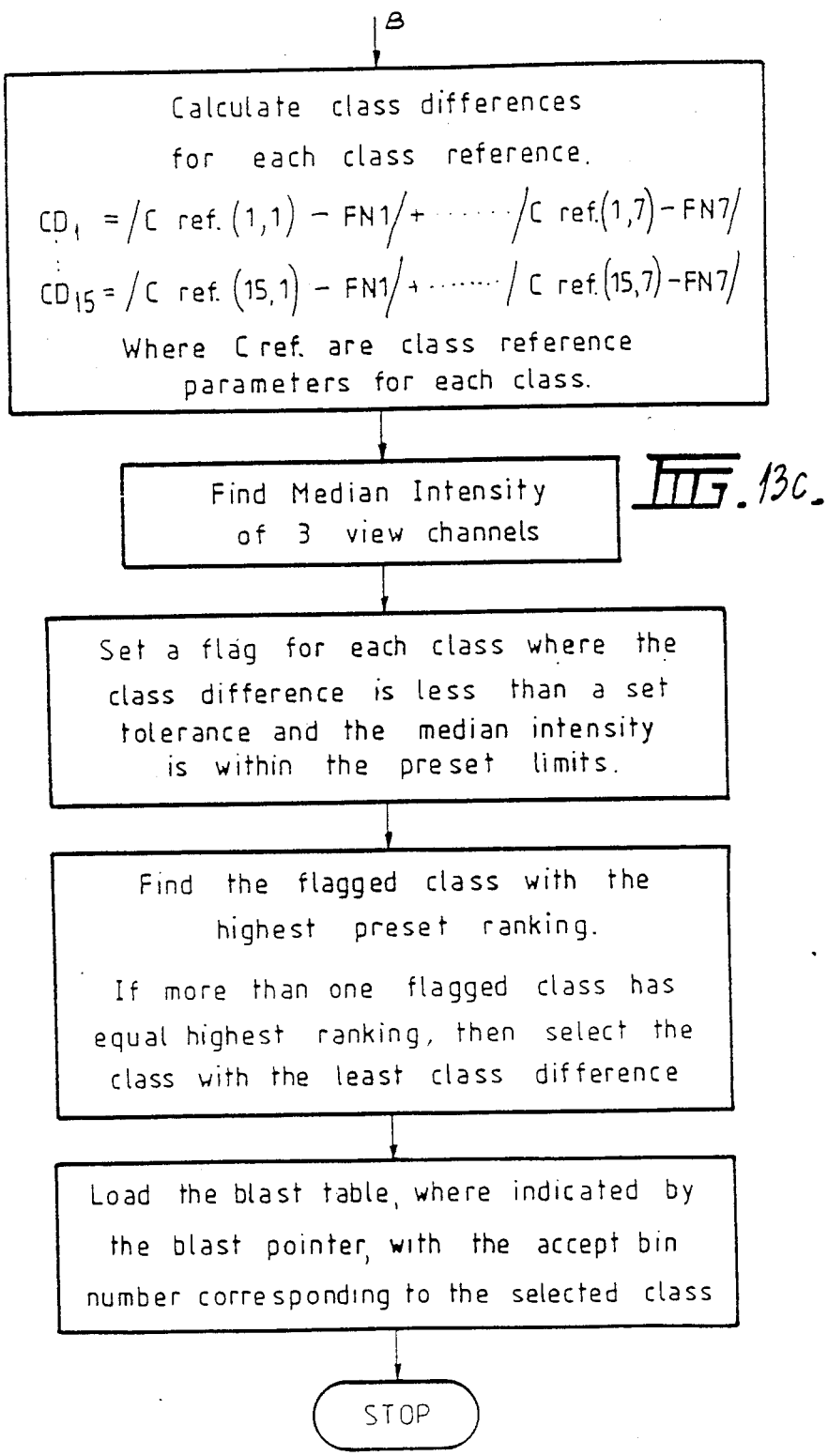
Figure 13D:
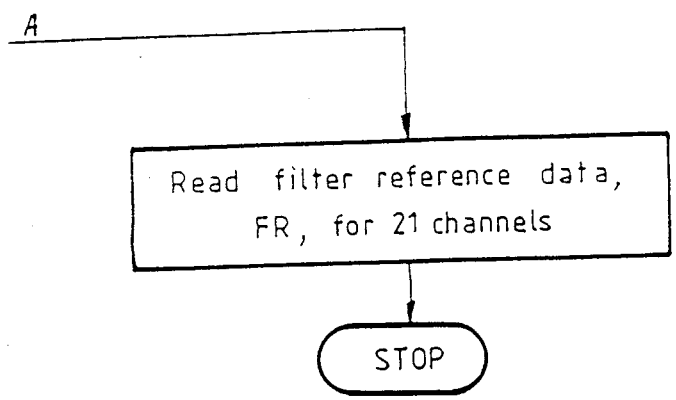
Figure 13F:
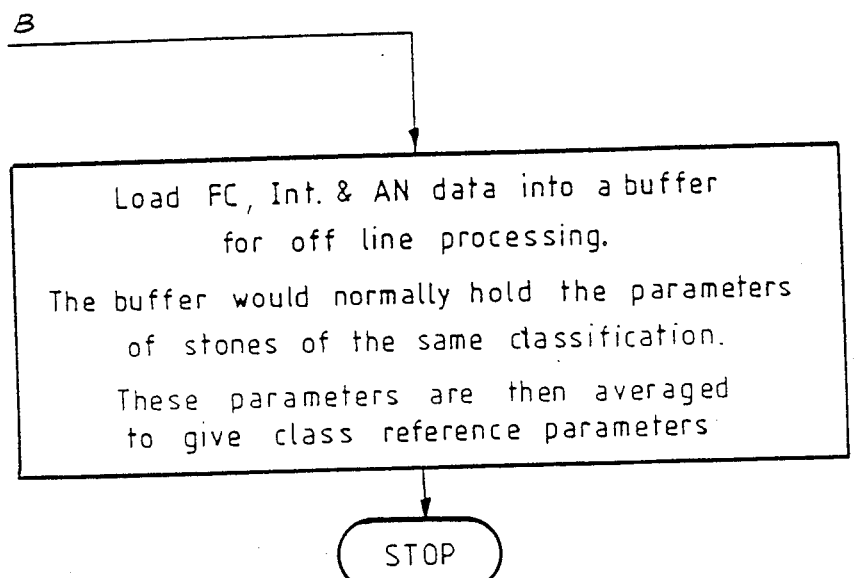

Particulars of the processor and its mode of operation will now be described with reference to FIGS. 11 to 13. FIG. 11 illustrates the signal forms obtained during area measurements, the first form corresponding to a no-stone position and the second form when a stone is in view. FIG. 12 illustrates the signal forms obtained during colour measurements, the first form corresponding to the measurement of the white reference and the second smaller form being that obtained when a stone is in view. FIG. 13 is a flow sheet for the classification routines.

(a) Area Measurements

The signal forms are shown in FIG. 11.

All area signals are outputs from area channel detectors covering the 3 views.

READ IR (infrared) channel background (ARO) with no stone and no IR emission.

READ Stone background (AO) which is area channel response with stone but no IR emission.

Switch on pulse of IR radiation, with stone in view, so that partial obscuration of IR background is measured as reduced response due to the obscuration, i.e.

$$\text{Area value } AN = (AR - AC)/AR$$
$$= 1 \text{ if no stone in field of view.}$$

(b) Colour Measurements

The signal forms are shown in FIG. 12.

For each of 3 views, on all 7 colour channels (21 measurements), the response for a particular stone is referenced to a white standard reading which is taken once per wheel revolution.

OBTAIN FR by subtracting offset (FO) from total reference signal.

OBTAIN F for each stone (each view and each of 7 colours) by subtracting FO from total colour signal.

COMPUTE colour level, $FC=F/FR$.

COMPUTE total "intensity" value, for purpose of grey-level separation, by summing the 7 colour values for a particular view, $$SFC = FC1 + FC2 + \cdots + FC7$$

then normalizing for area, $$INT(\text{ensity}) = (SFC/AN) \times 1000/7$$

A printout of F data gives area—normalized values of $(FC/AN) \times 1000$.

(c) Learn Mode

In LEARN mode, for each pre-identified stone type, and colour group, classification parameters are obtained.

For each acceptable view (i.e. areas of stones within preset limits),
 COMPUTE average values for area—normalized components F1 to F7, and
 (ii) COMPUTE colour tolerances and extract maximum and minimum intensity values.

For each colour component, FC, COMPUTE normalized colour value, $FN=(FC/SFC) \times 7000$.

In LEARN mode, each view of each stone is taken as a separate stone. The sum of differences of worst values from the average (reference) values (the Class Difference) is then labelled the TOLERANCE for that class.

(d) Edit Mode

In EDIT mode, the learned classification parameters can be manually modified from the keyboard if required, and colour classes can be appropriately labelled. Each class is ranked from 1 to 5, and allocated a product bin (1 to 4 plus R for reject).

The rank value is used along with tolerance and sum of class differences to determine the best class to which an unknown stone should be assigned.

(e) Classify Mode

In CLASSIFY mode, the following sequence is carried out to place appropriately an unknown stone. "Select Best Class"

Find in tolerance class with highest ranking—both in colour tolerance and within intensity max and min. (The intensity value for an unknown stone is selected as the median value of the 3 values generated by the 3 views).

If more than one permissible class is found, then find the class with the least class difference when compared with the unknown stone—computed as described above.

If no class is found which is "within tolerance" for a given unknown stone, then that stone is allowed to pass, undeflected, to reject.

A flow sheet for the classification routines is shown in FIG. 13.

The illustrated apparatus has been used successfully to sort and classify diamonds. However, this particular apparatus has been advanced by way of example only and it could be modified considerably. For example other optical examination systems could be used with a similar feed system providing accurate positioning and feeding of the stones. In one alternative optical system, a collimated light beam could be directed into the interior of the rotating suction wheel and reflected by an internal mirror out through the suction ports. An external light detector could then make a diffuse transmission measurement. An appropriate light collimator could be mounted in the hub of the wheel in addition to the suction connection by means of a double rotating vacuum seal.

In another optical measurement system, the rim of the vacuum wheel could project into a silica-walled cell containing an index-matching liquid and a beam of light could be directed through that cell onto the stones as they move through the cell. An optical detector could then be used to obtain a direct spectral transmission measurement.

The presentation and self-learning processing system can be used for rapid shape/including recognition in diamonds. Microscopic viewing based on a television scan of suitably illuminated diamonds can generate digital signals which can be used to separate shape/inclusion categories in a similar way to the colour separation in the illustrated example.

INDUSTRIAL APPLICABILITY

The invention is particularly applicable to the classification of diamonds. However, it may also be applied to the classification of other particulate materials such as gem stones of various kinds, mineral ores or even grain or food particles. Classification may be based on recognition of colour, shape, inclusions or any other measurable attributes of the particles concerned.

We claim:

1. Apparatus for classifying particulate material according to randomly variable attributes of the particles of that material, comprising:

particle feed means for feeding particulate material to be classified particle by particle along a feed path;

inspection means for inspecting each particle fed along the feed path and for deriving signals which are a measure of values of said attributes of that particle;

signal processing means having means for (a) storing a plurality of sets of specific values of attributes, each set of which is typical of one of a plurality of particulate classes within which the particulate material is to be classified, (b) establishing a range of values about each stored set of values determining a tolerance range of values for the respective particular class of which the stored set is typical, (c) applying rankings to the particular classes, (d) comparing each subsequently measured set of values of attributes of successive particles with the tolerance ranges of values for said particular classes and determining the highest ranking class having a tolerance range of values embracing said measured set of values, (e) operating in response to said measured set of values falling within the tolerance ranges of a plurality of said classes of equal ranking to compare differences between the specific values of the measured sets of values and the stored values of each of said plurality of classes of equal ranking to determine a closest match with one of said plurality of classes of equal ranking, and (f) outputting a signal representative of the highest ranking class having a tolerance range of values embracing said measured set of values if there is only one such class, or the determined closest matching class if said measured set of values falls within the tolerance ranges of a plurality of said classes of equal ranking; and classifier means operable in response to receiving said signal outputted by said signal processing means for directing the particles from said path selectively to multiple outlets, whereby the particulate material is classified.

2. Apparatus as claimed in claim 1 wherein the processing means includes means for enabling the said plurality of sets of specific values to be stored by feeding pre-sorted particles through the system, whereby said specific values are derived by the inspection means operating on those pre-sorted particles.

3. Apparatus as claimed in claim 1, wherein said attributes comprise the presence of particular colour characteristics when the particles are viewed from a plurality of directions, each colour characteristic being measured by a selective response to a particular wavelength or wavelength band in the visible spectrum.

4. Apparatus as claimed in claim 1, wherein the inspection means comprises a plurality of optical viewing means for viewing the particles in a plurality of directions at an inspection zone along said path, each optical viewing means providing a selective response to a particular wavelength or wavelength band in the visible spectrum, and wherein each selective response of each viewing means is a measure of one of said attributes.

5. Apparatus as claimed in claim 4, wherein the inspection means further comprises illumination means to illuminate the particles at the inspection zone such that light can be selectively absorbed by each particle according to its colour and re-emitted and the optical viewing means is responsive to such re-emitted light.

6. Apparatus as claimed in claim 4 wherein there are three of said optical viewing means to view the particles in directions 120° apart.

7. Apparatus as claimed in claim 4, wherein each optical viewing means comprises a series of optical fibres to receive re-emitted light from a particle under inspection and to direct that light through a corresponding series of differing colour filters to a series of light detectors whereby to provide the selective colour response.

8. Apparatus as claimed in claim 4 wherein each optical viewing means is inherently exposed to a white reference standard and means is provided to normalize the selective colour responses of the viewing means to the white reference response.

9. Apparatus as claimed in claim 1, wherein the particle feed means comprises a rotary feed structure rotatable about an axis and provided with a plurality of suction ports spaced circumferentially about the axis of rotation, suction means to apply suction to the suction ports during rotation of the rotary feed structure, and particle presentation means to receive a body of particles and to present particles from the body to the suction ports of the rotary structure such that individual particles are held to the suction ports by suction and transported by the rotary movement of the feed structure in an arcuate path constituting said feed path and wherein the classifier means comprises particle ejection means operable selectively to disrupt the application of suction to the suction ports and to apply fluid under pressure thereto whereby to eject particles therefrom selectively to said multiple outlets.

10. Apparatus for classifying particulate material, comprising:

particle feed means to feed particulate material to be classified particle by particle along a feed path;

inspection means to inspect each particle fed along the feed path and to derive signals which are a measure of a plurality of attributes of that particle;

signal processing means having means to store a plurality of sets of specific values of attributes, each set of which is typical of one of a plurality of particular classes into which the particulate material is to be classified, and means for (a) comparing subsequently measured sets of values of attributes of successive particles with the stored sets, (b) determining a closest match with one of said particular classes, and (c) outputting a signal representative of said closest match; and classifier means operable in response to receiving said signal outputted by said signal processing means for directing the particles from said path selectively to multiple outlets, whereby the particulate material is classified;

said inspection means including;
- (i) a plurality of optical viewing means for viewing the particles in a plurality of directions at an inspection zone along said path, each optical viewing means providing a selective response to a particular wavelength or wavelength band in the visible spectrum, and wherein each selective response of each viewing means is a measure of one of said attributes;
- (ii) infra-red emission means located such that each particle under inspection is viewed by each optical viewing means against a background of infra-red radiation, the optical viewing means also each providing a selective response to infra-red radiation as a measure of the viewed particle area, and
- (iii) means for modifying the selective color responses of each said viewing means according to the infra-red response of that viewing means to normalize the responses for particle size.

11. Apparatus for classifying particulate material, comprising:

particle feed means to feed particulate material to be classified particle by particle along a feed path;

inspection means to inspect each particle fed along the feed path and to derive signals which are a measure of a plurality of attributes of that particle;

signal processing means having means to store a plurality of sets of specific values of attributes, each set of which is typical of one of a plurality of particular classes into which the particulate material is to be classified, and means for (a) comparing subsequently measured sets of values of attributes of successive particles with the stored sets, (b) determining a closest match with one of said particular classes, and (c) outputting a signal representative of said closest match; and classifier means operable in response to receiving said signal outputted by said signal processing means for directing the particles from said path selectively to multiple outlets, whereby the particulate material is classifed;

said particle feed means including;
- (a) a rotary feed structure rotatable about an axis and provided with a plurality of suction ports spaced circumferentially about the axis of rotation;
- (b) suction means for applying suction to the suction ports during rotation of the rotary feed structure; and
- (c) particle presentation means for receiving a body of ports of the rotary structure such that individual particles are held to the suction ports by suction and transported by the rotary movement of the feed structure in an arcuate path constituting said feed path, and wherein said classifier means includes (i) particle ejection means comprising a plurality of valves each associated with one of the suction ports and each operable by application of fluid under pressure to cut off the application of suction to the associated port and to apply said fluid under pressure to the port, and (ii) means selectively to apply fluid under pressure to the valves whereby to cause ejection of particles from the ports to said multiple outlets by expulsion of fluid under pressure through selected ports.

12. Apparatus for classifying particulate material, comprising:

particle feed means for feeding particulate material to be classified, particle by particle, along a feed path;

inspection means for inspecting each particle fed along the feed path and for deriving signals which are a measure of a plurality of attributes of that particle;

classifier means operable to direct the particles from said path selectively to multiple outlets; and control means for controlling operation of the classifier means in accordance with the signals derived from the inspection means, and wherein said inspection means includes
- (i) optical viewing means for viewing particles in a plurality of directions at an inspection zone along said path, said optical viewing means comprising a plurality of optical viewers each providing a selective response to a particular wavelength or wavelength band in the visible spectrum and wherein each selective response of each viewer is a measure of one of said attributes,
- (ii) infra-red emission means located such that each particle under inspection is viewed by each optical viewer against a background of infra-red radiation,
- (iii) said optical viewers also each provide a selective response to infra-red radiation as a measure of the viewed particle area, and
- (iv) means for modifying the selective color responses of each viewer according to the infra-red response of that viewer to normalize the responses for particle size.

* * * * *